United States Patent
Peters

(10) Patent No.: US 11,311,659 B2
(45) Date of Patent: Apr. 26, 2022

(54) BLOOD TREATMENT DEVICE COMPRISING A METERING LINE HAVING A MEMBRANE PUMP AND A VALVE AND METHOD FOR METERING

(71) Applicant: FRESENIUS MEDICAL CARE DEUTSCHLAND GMBH, Bad Homburg (DE)

(72) Inventor: Arne Peters, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 670 days.

(21) Appl. No.: 16/064,265

(22) PCT Filed: Dec. 20, 2016

(86) PCT No.: PCT/EP2016/002140
§ 371 (c)(1),
(2) Date: Jun. 20, 2018

(87) PCT Pub. No.: WO2017/108176
PCT Pub. Date: Jun. 29, 2017

(65) Prior Publication Data
US 2019/0022297 A1    Jan. 24, 2019

(30) Foreign Application Priority Data
Dec. 21, 2015   (DE) .................... 10 2015 016 670.0

(51) Int. Cl.
*A61M 1/36*   (2006.01)
*F04B 11/00*  (2006.01)
(Continued)

(52) U.S. Cl.
CPC ............ *A61M 1/367* (2013.01); *A61M 1/342* (2013.01); *A61M 1/3672* (2013.01);
(Continued)

(58) Field of Classification Search
CPC .... A61M 1/367; A61M 1/342; A61M 1/3672; A61M 2205/3334; A61M 60/851;
(Continued)

(56) References Cited

U.S. PATENT DOCUMENTS

| | | | |
|---|---|---|---|
| 6,604,908 B1 | 8/2003 | Bryant et al. | |
| 2009/0214364 A1* | 8/2009 | Wex | A61M 5/152 417/474 |
| 2013/0074959 A1 | 3/2013 | Demers et al. | |

FOREIGN PATENT DOCUMENTS

| | | |
|---|---|---|
| DE | 4118600 | 12/1992 |
| DE | 4228193 | 10/1993 |

(Continued)

OTHER PUBLICATIONS

Diaphragm Pump, https://en.wikipedia.org/wiki/Diaphragm_pump.

*Primary Examiner* — Leslie R Deak
(74) *Attorney, Agent, or Firm* — Jacobson Holman PLLC

(57) ABSTRACT

The invention relates to a blood treatment device having at least one metering line which opens into a fluid circuit, wherein a conveyor module is arranged in the metering line and comprises a membrane pump and a valve which is arranged at the pressure side thereof and which can act both as a blocking valve and as a restricting valve.

15 Claims, 2 Drawing Sheets

Figure 1:
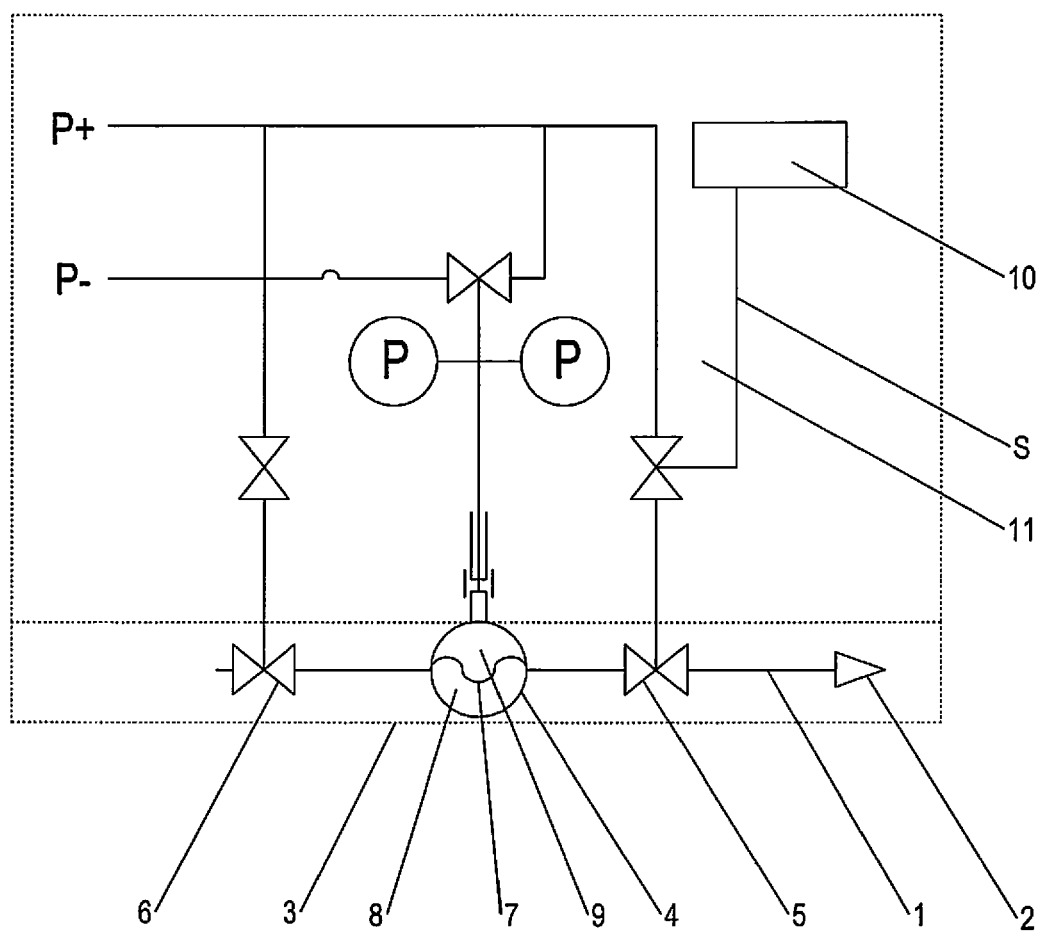

(51) Int. Cl.
    *F04B 13/00* (2006.01)
    *A61M 1/34* (2006.01)
    *F04B 49/22* (2006.01)
    *F04B 43/06* (2006.01)
    *A61M 60/40* (2021.01)

(52) U.S. Cl.
    CPC ......... *A61M 60/40* (2021.01); *F04B 11/0091* (2013.01); *F04B 13/00* (2013.01); *F04B 43/06* (2013.01); *F04B 49/225* (2013.01); *A61M 2205/3334* (2013.01); *F04B 2205/03* (2013.01); *F04B 2205/09* (2013.01); *F04B 2205/172* (2013.01)

(58) Field of Classification Search
    CPC ................ A61M 60/853; A61M 39/28; A61M 2039/2433; F04B 11/0091; F04B 13/00
    See application file for complete search history.

(56) References Cited

FOREIGN PATENT DOCUMENTS

| | | |
|---|---|---|
| DE | 102010007464 | 8/2011 |
| EP | 1746479 | 1/2007 |

\* cited by examiner

BLOOD TREATMENT DEVICE COMPRISING A METERING LINE HAVING A MEMBRANE PUMP AND A VALVE AND METHOD FOR METERING

The invention relates to a blood treatment device comprising a metering line having a membrane pump and a blocking and restricting valve.

The correct metering of fluids is of central importance in dialysis. Large fluid flows such as the flow of dialysis fluid are often conveyed via balancing systems. Medium-sized fluid flows such as the extracorporeal blood flow are often conveyed by hose roller pumps. Flow errors of up to approximately 10% are accepted in this respect.

There is, however, a higher demand on metering accuracy on the metering in of small quantities of an active agent solution, for example on the metering of an anticoagulant solution into the extracorporeal blood circuit. The flow error should in this respect be below 5% in every case. Hose roller pumps or syringe pumps are often used for this purpose in the prior art. The use of membrane pumps is, in contrast, not very prevalent in the prior art since unwanted flow pulses are generated.

The flow pulses are due to the fact that in membrane pumps the membrane influences the pressure balance which is ideally present between the two chambers of the membrane pump due to its elasticity, due to its deformation and due to its initial tension. The relationship $P_{PNEU} - P_{HYD} = P_{MEM}$ applies to a pneumatic membrane pump in a static case. The membrane pressure $P_{MEM}$ is not constant and therefore represents an interference factor in the regulation of the pump since the fluid pressure $P_{HYD}$ does not vary in proportion with the regulation pressure $P_{PNEU}$. The influence of this interference factor is large in a relative aspect when the fluid pressure $P_{HYD}$ and the regulation pressure $P_{PNEU}$ are low. This is the case, for example, when small flow rates are to be generated using the membrane pump.

However, a constant flow above all has to be maintained on the administration of citrate as the anticoagulant.

It is the object of the invention also to reduce the influence of this disruptive factor at small flow rates.

Against this background, the invention relates to a blood treatment device having at least one metering line which opens into a fluid circuit, wherein a conveyor module is arranged in the metering line and comprises a membrane pump and a valve arranged at the pressure side thereof. The valve is configured such that it can act both as a blocking valve and as a restricting valve.

The underlying idea of the invention comprises increasing the flow resistance by a reduction of the flow cross-section downstream of the pump and thus generating a pressure offset for the fluid pressure $P_{HYD}$ (and consequently for the regulation pressure $P_{PNEU}$) which reduces the influence of the unchanging membrane pressure $P_{MEM}$. The flow of the conveyed fluid can thereby be smoothed and small flows can also be regulated. There are further advantages in that less elastic plastics, and therefore optionally less expensive plastics, can be used for the construction of the pump membrane and in that the geometry of the membrane is less decisive.

In an embodiment, the blood treatment device is a dialysis device.

In an embodiment, the metering line is a metering line for a solution of a coagulation-inhibiting agent which opens into an extracorporeal blood circuit of the blood treatment device.

In an embodiment, the membrane pump is a pneumatically operated membrane pump. In an embodiment, the valve is a pneumatically operated valve. If both the pump and the valve are pneumatically operated, provision can be made that the two actuators are connected to a common pneumatic module. The valve is preferably configured such that its closed state is proportional to the pneumatic pressure.

In an embodiment, the membrane pump and the valve are arranged in a common housing of the conveyor module. Provision can be made that the housing comprises at least two parts releasably fastened to one another, wherein a first part comprises the pump mechanism and the valve mechanism and a second part defines at least one section of the fluid-conveying metering line. The first part can be a reusable unit and the second part can be a disposable unit releasably placed into the reusable unit.

In an embodiment, the blood treatment device has a control unit which controls the pump and the valve, preferably by means of the pneumatic module. In this respect, an algorithm is stored on the control unit and is designed such that the flow cross-section in the valve is reduced with respect to the maximum flow cross-section during a pressure phase of the pump to increase the flow resistance and thus to generate a counter-pressure in the fluid chamber of the pump. The flow cross-section can, for example, be reduced by half or by more than half. It can thus be achieved that the pressure offset is significantly higher than the interfering membrane pressure $P_{MEM}$, for example at least three times higher.

In an embodiment, the algorithm stored on the control unit is furthermore designed such that the reduced flow cross-section in the valve is continuously increased during the pressure phase, of the pump in order to ensure a constant flow rate from the conveyor module during a reducing fluid pressure in the pump. Provision can furthermore be made in this respect that the pneumatic volume in the regulation chamber of the pump is kept constant during the pressure phase of the pump. In this embodiment, the regulation pressure $P_{PNEU}$ only varies due to the fluid displaced from the pump chamber. The flow rate of the fluid can be regulated precisely by means of the opening state of the valve.

In an embodiment, the algorithm stored on the control unit is furthermore designed such that the reduced flow cross-ssection in the valve and the fluid pressure in the pump are kept constant during the pressure phase of the pump in order to ensure a constant flow rate from the conveyor module. In this embodiment, for example, the pneumatic volume behind the membrane is actively regulated to keep the regulation pressure $P_{PNEU}$ constant with a varied volume on the fluid side and to be able to precisely regulate the flow rate of the fluid with an unchanging opening state of the valve by means of the regulation pressure.

To obtain information on the fluid flow or on the pressures suitable for the regulation, flow sensors and/or pressure sensors which are connected to the control unit can be arranged both in the fluid system and in the pneumatic system.

In an embodiment, the conveyor module furthermore comprises a blocking valve at the suction side which is preferably arranged in the same housing as the membrane and the valve at the pressure side and/or which is connected to the same pneumatic module. The suction-side blocking valve can have an identical design to the pressure-side restricting valve. It can be controlled by the control unit, preferably by means of the pneumatic module, such that it is closed during the pressure phase of the pump.

The present invention furthermore relates to a method for metering a medium such as an active agent which is preferably carried out in a blood treatment device in accordance with the following description. The method preferably relates to the metering of at least one active agent such as of an anticoagulant into a fluid flow or into a fluid which is e.g. a dialysis fluid or a fluid from which the dialysis fluid is prepared. The method is characterized in that a conveyor module located in a metering line is used for the metering, said conveyor module comprising a membrane pump and a valve arranged at the pressure side thereof which can act both as a blocking valve and as a restricting valve.

Further advantageous aspects of the method are described below.

It is conceivable that the pump and the valve are preferably controlled by means of a pneumatic module such that the flow cross-section in the valve is reduced with respect to the maximum flow cross-section during a pressure phase of the pump to increase the flow resistance and thus to generate a counter-pressure in the fluid chamber of the pump.

Provision is made in a preferred embodiment that the reduced flow cross-section in the valve is continuously increased during the pressure phase of the pump in order to ensure a constant flow rate from the conveyor module during a reducing fluid pressure in the pump.

It is furthermore conceivable that the pneumatic volume in the regulation chamber of the pump is kept constant during the pressure phase of the pump.

Provision is made in a further embodiment of the method that the reduced flow cross-section in the valve and fluid pressure in the pump are kept constant during the pressure phase of the pump to ensure a constant flow rate from the conveyor module.

Figure 2:
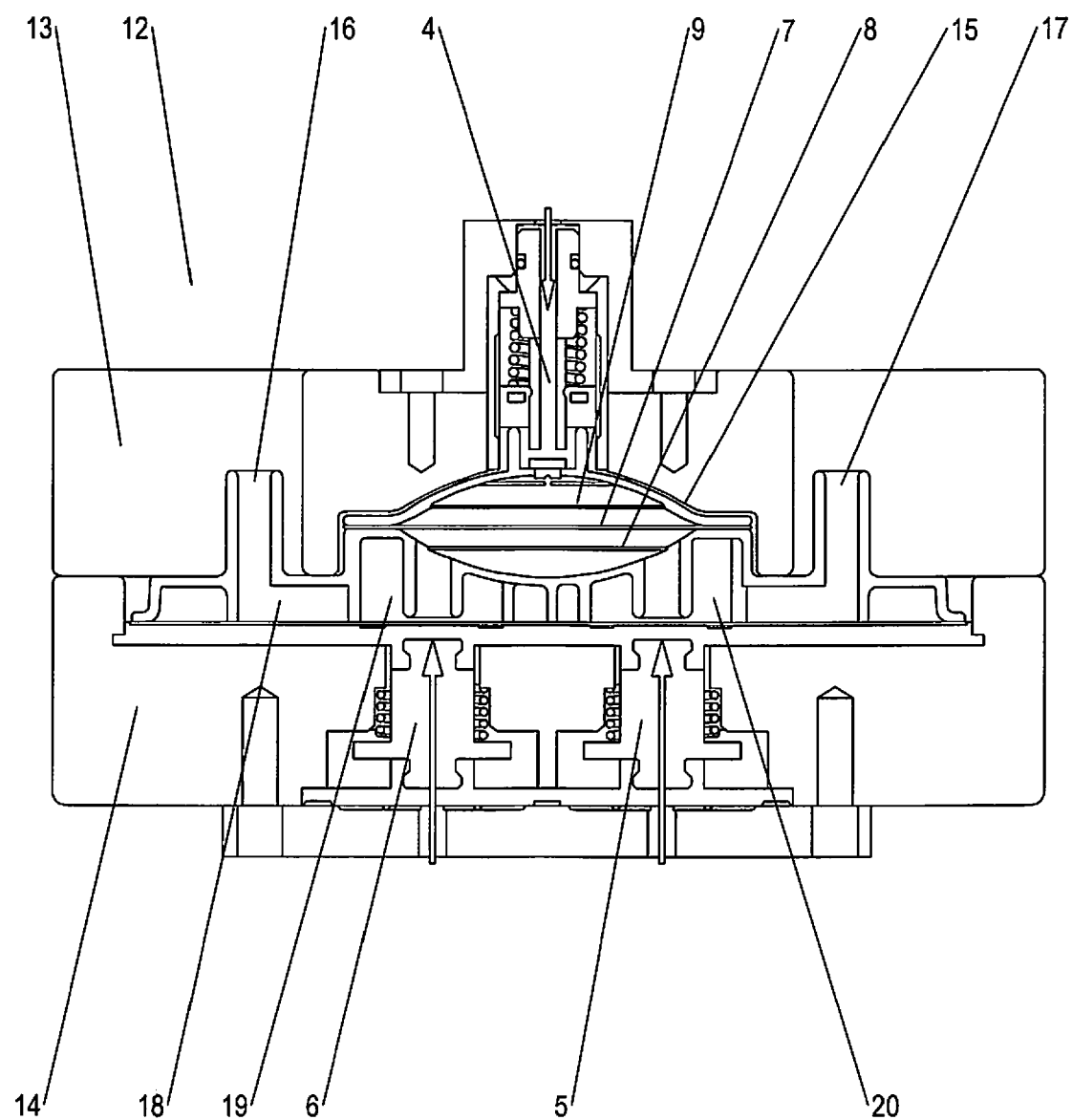

Further details and advantages of the invention result from the embodiments described in the Figures. There are shown in the Figures:

FIG. 1: a schematic representation of a conveyor module of a blood treatment device in accordance with the invention; and FIG. 2: a cross-section through an embodiment of a conveyor module of a blood treatment device in accordance with the invention.

A conveyor module of a blood treatment device in accordance with the invention is shown schematically in FIG. 1 which is arranged at a metering line 1 of a blood treatment device. In the embodiment shown, it is a metering line 1 for an anticoagulant of a dialysis device which is connected at the suction side to a reservoir for an anticoagulant solution and at the pressure side to the extracorporeal blood circuit of the device. The conveyor module is marked by the reference numeral 3, the direction of flow of the anticoagulant solution in the metering line 1 by the reference numeral 2.

The conveyor module 3 comprises a membrane pump 4, a valve 5 arranged at the pressure side and a valve 6 arranged at the suction side. The valves 5 and 6 are identical and can both interrupt the fluid flow (that is can act as a blocking valve) and reduce the flow cross-section (that is can act as a restricting valve). Provision is preferably made that the valves 5 and 6 can continuously reduce the flow cross-section of the metering line 1.

The membrane pump 4 is pneumatic and comprises a pump membrane 7 which is arranged between a fluid chamber 8 for the fluid 8 to be conveyed and a pneumatic regulation chamber 9. A pneumatic regulation pressure $P_{PNEU}$ is present in the regulation chamber 9 in the operation of the pump and a fluid pressure $P_{HYD}$ is present in the fluid chamber 8 in operation. As was initially explained, a membrane pressure $P_{MEM}$ also emanates from the membrane 7 and interferes with the balance which is present in the ideal case between the regulation pressure $P_{PNEU}$ and the fluid pressure $P_{HYD}$.

The membrane pump 4 and the two valves 5 and 6 are controlled by a pneumatic module 11 which is connected to a control unit 10 and which is shown in FIG. 1 by the region above the conveyor module 3 in a light shade. Flow sensors and pressure sensors, not shown, in the pneumatic lines and in the fluid line 1 are likewise connected to the control unit and deliver data which are of importance for the regulation of the conveyor module 3.

Reference symbol S marks a control line from the control unit 10 to a valve of the pneumatic module 11 which in turn controls the valve 5.

An algorithm is stored on the control unit and is designed so that the flow cross-section in the pressure-side valve 5 for the fluid to be conveyed is reduced with respect to the maximum flow cross-section during a pressure phase of the pump 4 (that is with a closed suction-side valve 6 and a pressure increase in the regulation chamber 9). The flow resistance at the pressure-side valve 5 is thus increased and a counter-pressure is generated in the fluid chamber 8 of the membrane pump 4. This offset for the fluid pressure in the fluid chamber 8 (and consequently for the regulation pressure in the regulation chamber 9) reduces the significance of the membrane pressure which remains unchanged due to this measure, whereby the proportionality of the fluid pressure development and of the regulation pressure development is improved.

In order to generate a constant flow on the pressure side of the conveyor module 3 under these conditions, provision can be made that the algorithm stored on the control unit 10 is designed such that the pneumatic volume in the regulation chamber 9 of the membrane pump 4 is kept constant during the pressure phase of the pump. The fluid pressure in the fluid chamber 8 and corresponding thereto the regulation pressure in the regulation chamber 9 are thereby gradually reduced due to the fluid running out of the fluid chamber 8. In order in this respect to be able to keep the flow rate of the fluid at the pressure side of the conveyor module 3 constant, the algorithm stored on the control unit 10 is designed such that the flow cross-section in the pressure-side valve 5 is continuously increased as the fluid pressure in the fluid chamber 8 reduces.

Provision can alternatively be made that the algorithm stored on the control unit 10 is designed such that the flow cross-section in the pressure-side valve 5 is kept constant during the pressure phase of the pump so that a constant offset pressure is generated in the fluid chamber 8. To be able to keep the flow rate of the fluid constant on the pressure side of the conveyor module 3, the regulation pressure during the pressure phase of the pump 4 is kept constant by a continuous increase of the pneumatic volume in the regulation chamber 9.

FIG. 2 shows a cross-section through a conveyor module 3 of a blood treatment device in accordance with the invention, wherein components already shown schematically in FIG. 1 are marked by identical reference numerals.

As can be seen from this Figure, the conveyor module comprises a housing 12 which comprises two oppositely disposed machine plates 13 and 14 as well as a removable disposable unit 15 arranged therebetween. The pump 4 is countersunk in a cut-out of a first machine plate 13 and the two valves 5 and 6 are countersunk in cut-outs in the second machine plate 14 so that the pump mechanism and the valve mechanism are arranged on oppositely disposed sides of the disposable unit 15.

The disposable unit 15 is configured in multiple parts and comprises a silicone disk contacting the valve-carrying plate 14 and a molded silicone part contacting the pump-carrying plate 13. It comprises a suction-side connector 16 as well as a pressure-side connector 17 between which a fluid vessel 18 is arranged. The fluid vessel 18 forms the valve chamber 19 of the suction-side valve 6, the fluid chamber 8 of the membrane pump 4 as well as the valve chamber 20 of the pressure-side valve 5. The regulation chamber 9 of the membrane pump 4 is also formed by the disposable unit 15.

The total fluid path 1 is thus completely surrounded by the disposable unit 1, whereby a contamination of the machine-side parts is prevented.

In summary, it results that a higher pump accuracy can be achieved in a blood treatment device in accordance with the invention by production of an offset pressure in the fluid chamber 8 of a membrane pump 4 arranged in a metering line 1. The offset pressure is generated by a direct control of a blocking valve and restricting valve 5 which is arranged at the pressure side of the pump and which can be adaptively regulated.

The invention claimed is:

1. A blood treatment device having
   at least one metering line having an opening into a fluid circuit,
   a conveyor module arranged in the metering line and comprising a membrane pump having a pressure side and a valve which is arranged on the pressure side and which can act both as a blocking valve and as a restricting valve by changing the valve flow cross-section, and
   a control unit which controls the pump and the valve such that the flow cross-section in the valve is reduced with respect to the maximum flow cross-section during a pressure phase of the pump in order to increase the flow resistance and thus to generate a counter-pressure in a fluid chamber of the pump.

2. A blood treatment device in accordance with claim 1, characterized in that the blood treatment device is a dialysis device.

3. A blood treatment device in accordance with claim 1, characterized in that the metering line is a metering line for a solution of a coagulation-inhibiting agent which opens into an extracorporeal blood circuit of the blood treatment device.

4. A blood treatment device in accordance with claim 1, characterized in that the membrane pump and/or the valve is/are operated pneumatically and is/are preferably connected to a common pneumatic module.

5. A blood treatment device in accordance with claim 1, characterized in that the membrane pump and the valve are arranged in a common housing of the conveyor module.

6. A blood treatment device in accordance with claim 5, characterized in that the housing comprises at least two parts which are releasably fastened to one another, wherein a first part comprises the pump mechanism and the valve mechanism and a second part defines at least one section of a fluid-conducting vessel of the metering line.

7. A method for metering a medium, preferably in a blood treatment device in accordance with claim 1, comprising metering the medium into the fluid circuit through the conveyor module located in the metering line during a pressure phase of the pump while reducing the maximum flow cross-section in the valve in order to increase flow resistance and thus to generate a counter-pressure in the fluid chamber of the pump.

8. A method in accordance with claim 7, characterized in that the pump and the valve are controlled by the pneumatic module.

9. A method in accordance with claim 7, comprising continuously reducing the flow cross-section during the pressure phase of the pump in order to ensure a constant flow rate from the conveyor module as the fluid pressure in the pump reduces.

10. A method in accordance with claim 9, characterized in that the pneumatic volume in a regulation chamber of the pump is kept constant during the pressure phase of the pump.

11. A method in accordance with claim 7, characterized in that the reduced flow cross-section in the valve and the fluid pressure in the pump are kept constant during the pressure phase of the pump to ensure a constant flow rate from the conveyor module.

12. A blood treatment device in accordance with claim 1, wherein the control unit controls the pump and the valve by means of the pneumatic module.

13. A blood treatment device in accordance with claim 1, characterized in that the control unit is configured such that the reduced flow cross-section in the valve is continuously increased during the pressure phase of the pump in order to ensure a constant flow rate from the conveyor module as the fluid pressure reduces.

14. A blood treatment device in accordance with claim 13, characterized in that the control unit is configured such that the pneumatic volume in a regulation chamber of the pump is kept constant during the pressure phase of the pump.

15. A blood treatment device in accordance with claim 1, characterized in that the control unit is configured such that the reduced flow cross-section in the valve and the fluid pressure in the pump are kept constant during the pressure phase of the pump to ensure a constant flow rate from the conveyor module.

* * * * *